(12) United States Patent
Zeikus

(10) Patent No.: US 7,819,576 B2
(45) Date of Patent: *Oct. 26, 2010

(54) PNEUMATIC BIOREACTOR

(75) Inventor: J. Gregory Zeikus, Okemos, MI (US)

(73) Assignee: PBS Biotech, Inc., Caamarillo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/606,519

(22) Filed: Oct. 27, 2009

(65) Prior Publication Data

US 2010/0041095 A1 Feb. 18, 2010

Related U.S. Application Data

(63) Continuation of application No. 11/258,742, filed on Oct. 26, 2005, now Pat. No. 7,628,528.

(51) Int. Cl.
B26D 7/06 (2006.01)

(52) U.S. Cl. .................. 366/102; 366/325.93

(58) Field of Classification Search .................. 366/102, 366/325.93, 325.92; 261/84, 191; 210/150
See application file for complete search history.

(56) References Cited

U.S. PATENT DOCUMENTS

| 29,149 A | 7/1860 | Durham |
|---|---|---|
| 211,143 A | 1/1879 | Fogarty |
| 257,505 A | 5/1882 | McMilan et al. |
| 271,040 A | 1/1883 | Cook |
| 272,656 A | 2/1883 | Cook |
| 384,568 A | 6/1888 | Evans |

(Continued)

FOREIGN PATENT DOCUMENTS

EP 0249433 A1 12/1987

(Continued)

OTHER PUBLICATIONS

Singapore (Australian) Cover Sheet, Search Report, Written Opinion, and Citation Annexes for corresponding Singapore Patent Application No. SG 200802702-1, 7 pages (mailed Apr. 28, 2009).

(Continued)

*Primary Examiner*—Tony G Soohoo
(74) *Attorney, Agent, or Firm*—Rothwell, Figg, Ernst & Manbeck, PC

(57) ABSTRACT

A pneumatic bioreactor includes a vessel containing a fluid to be mixed and at least one mixing device driven by gas pressure. A first embodiment includes a floating impeller that rises and falls in the fluid as gas bubbles carry it upward to the surface where the gas is then vented, permitting the impeller to sink in the fluid. The floating impeller may be tethered to a second impeller with a flexible member and pulley. The mixing speed is controlled with electromagnets in the vessel acting upon magnetic material in the impeller or its guides. In another embodiment, floating pistons mix the fluid, pushing it through a mixing plate with one or more apertures. In a third embodiment, the mixing device is a rotating drum with bubble-catching blades and rotating mixing plates with apertures. The top of the vessel for these mixers may include a closed top and sterile filters.

11 Claims, 7 Drawing Sheets

U.S. PATENT DOCUMENTS

| | | | |
|---|---|---|---|
| 650,063 A | 5/1900 | Kerten | |
| 3,498,762 A | 3/1970 | Van Der Schee et al. | |
| 3,715,885 A | 2/1973 | Schur | |
| 3,722,185 A | 3/1973 | Miczek | |
| 3,786,781 A * | 1/1974 | Poulsen | 119/246 |
| 3,788,616 A | 1/1974 | Clough, Jr. | |
| 3,886,074 A | 5/1975 | Prosser | |
| 3,911,064 A | 10/1975 | McWhirter et al. | |
| 3,930,816 A | 1/1976 | Miczek | |
| 3,990,870 A | 11/1976 | Miczek | |
| 4,053,141 A | 10/1977 | Gussefeld | |
| 4,054,031 A | 10/1977 | Johnson | |
| 4,095,426 A | 6/1978 | Rhodes | |
| 4,101,384 A | 7/1978 | Faust et al. | |
| 4,160,736 A * | 7/1979 | Prosser | 210/150 |
| 4,170,114 A | 10/1979 | Pruett | |
| 4,196,590 A | 4/1980 | Fries | |
| 4,203,961 A | 5/1980 | Cowley | |
| 4,223,094 A | 9/1980 | Vaseen | |
| 4,245,473 A | 1/1981 | Sandoval | |
| 4,246,753 A | 1/1981 | Redmond | |
| 4,266,402 A | 5/1981 | Pruett | |
| 4,268,385 A * | 5/1981 | Yoshikawa | 210/150 |
| 4,284,503 A * | 8/1981 | Stahler | 210/150 |
| 4,326,132 A | 4/1982 | Bokel | |
| 4,363,212 A | 12/1982 | Everett | |
| 4,416,546 A | 11/1983 | Parkins | |
| 4,540,491 A * | 9/1985 | Zimmer | 210/619 |
| 4,595,296 A | 6/1986 | Parks | |
| 4,655,603 A | 4/1987 | Palm | |
| 4,668,387 A | 5/1987 | Davis | |
| 4,779,990 A | 10/1988 | Hjort | |
| 4,919,849 A | 4/1990 | Litz | |
| 4,944,598 A | 7/1990 | Steele | |
| 4,956,082 A | 9/1990 | Choi | |
| 5,075,234 A | 12/1991 | Tunac | |
| 5,081,035 A | 1/1992 | Halberstadt et al. | |
| 5,156,778 A | 10/1992 | Small | |
| 5,198,156 A | 3/1993 | Middleton | |
| 5,326,459 A * | 7/1994 | Hlavach et al. | 210/150 |
| 5,570,517 A | 11/1996 | Luker | |
| 5,605,400 A | 2/1997 | Kojima | |
| 5,632,962 A | 5/1997 | Baker et al. | |
| 5,755,961 A * | 5/1998 | Limcaco | 210/416.2 |
| 5,755,976 A | 5/1998 | Kortmann | |
| 5,756,012 A | 5/1998 | McGlashan et al. | |
| 5,791,780 A | 8/1998 | Bakker | |
| 5,939,313 A | 8/1999 | Cheng | |
| 6,036,355 A | 3/2000 | Yant et al. | |
| 6,036,357 A | 3/2000 | Van Drie | |
| 6,135,629 A | 10/2000 | Dohmann | |
| 6,140,615 A * | 10/2000 | Matsumoto | 219/441 |
| 6,195,991 B1 | 3/2001 | De Shon | |
| 6,237,898 B1 | 5/2001 | Lafont | |
| 6,305,165 B1 | 10/2001 | Mizuki | |
| 6,361,202 B1 | 3/2002 | Lee et al. | |
| 6,392,072 B1 | 5/2002 | Henriksen | |
| 6,406,624 B1 | 6/2002 | Devos | |
| 6,439,756 B1 | 8/2002 | Forschner et al. | |
| 6,447,243 B1 | 9/2002 | Kittle | |
| 6,599,426 B2 | 7/2003 | Drie | |
| 6,673,532 B2 | 1/2004 | Rao | |
| 6,926,437 B2 | 8/2005 | Drie | |
| 7,083,324 B2 | 8/2006 | Van Drie | |
| 7,083,720 B2 | 8/2006 | Miller | |
| 7,201,884 B2 | 4/2007 | Cohen | |
| 7,628,528 B2 * | 12/2009 | Zeikus | 366/102 |
| 2002/0110915 A1 | 8/2002 | Shaaltiel | |
| 2003/0161216 A1 | 8/2003 | Gigas et al. | |
| 2005/0158851 A1 | 7/2005 | Furey | |
| 2005/0201202 A1 | 9/2005 | Drie | |
| 2005/0258083 A1 | 11/2005 | Miller | |
| 2005/0272146 A1 | 12/2005 | Hodge et al. | |

FOREIGN PATENT DOCUMENTS

| | | |
|---|---|---|
| EP | 0617120 A2 | 9/1994 |
| EP | 1120460 A1 | 8/2001 |
| JP | 60-164476 | 8/1985 |

OTHER PUBLICATIONS

International Search Report and Written Opinion for PCT Patent Application No. PCT/US2006/060183, 6 pages (mailed Aug. 21, 2008).

International Preliminary Report on Patentability for PCT Patent Application No. PCT/US2006/060183, 5 pages (mailed Sep. 16, 2008).

* cited by examiner

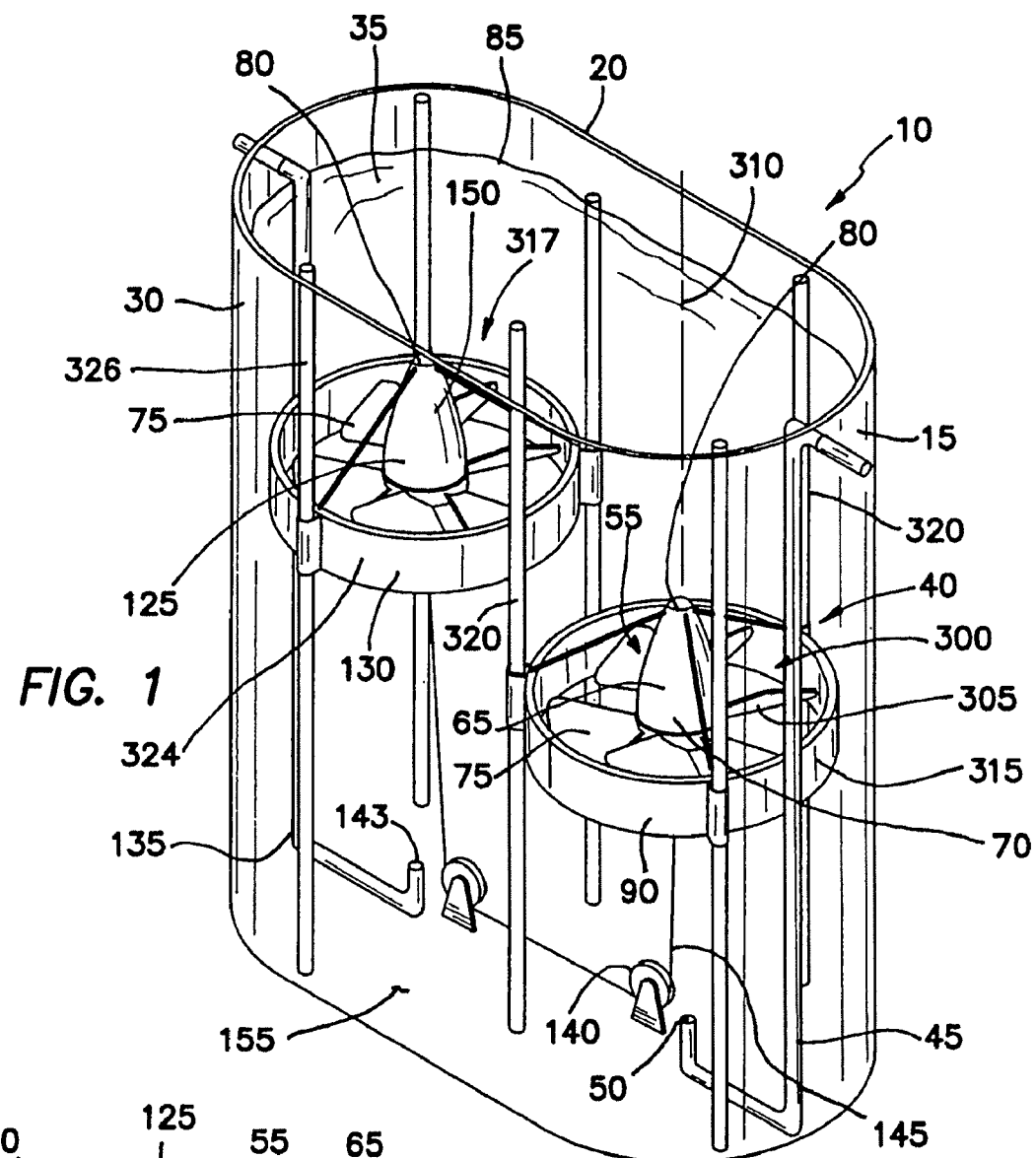

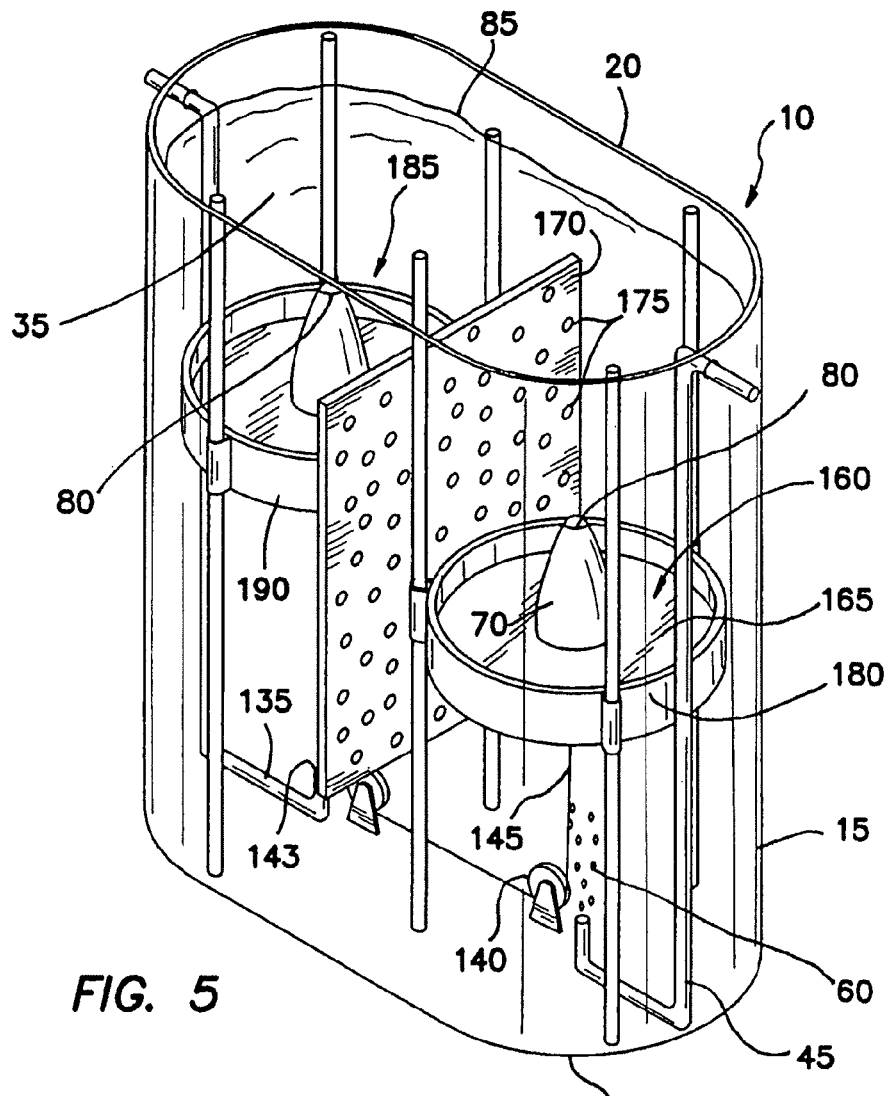
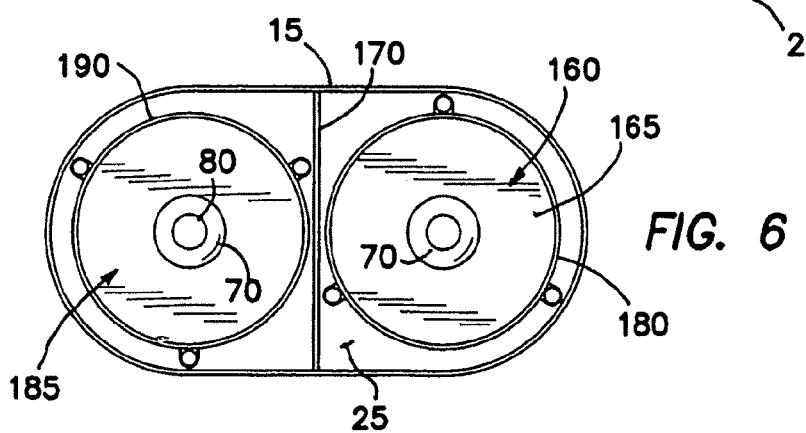

PNEUMATIC BIOREACTOR

CROSS-REFERENCE TO RELATED APPLICATION

This application is a continuation application claiming priority under 35 U.S.C. §120 of U.S. patent application Ser. No. 11/258,742, filed Oct. 26, 2005, now U.S. Pat. No. 7,628,528, the disclosure of which is hereby incorporated by reference.

FIELD OF INVENTION

The invention pertains to apparatus for mixing solutions. More particularly, the invention relates to pneumatically operated mixers for use in closed, sterile environments.

BACKGROUND OF THE INVENTION

Bioreactors have been used for cultivation of microbial organisms for production of various biological or chemical products in the pharmaceutical, beverage and biotechnological industry. A production bioreactor contains culture medium in a sterile environment that provides various nutrients required to support growth of the biological agents of interest. Conventional bioreactors use mechanically driven impellers to mix the liquid medium during cultivation. The bioreactors can be reused for the next batch of biological agents after cleaning and sterilization of the vessel. The procedure of cleaning and sterilization requires a significant amount of time and resources, especially, to monitor and to validate each cleaning step prior to reuse for production of biopharmaceutical products. Due to the high cost of construction, maintenance and operation of the conventional bioreactors, single use bioreactor systems made of disposable plastic material have become an attractive alternative.

While several mixing methods of liquid in disposable bioreactors have been proposed in recent years, none of them provides efficient mixing for large scale (greater than 1000 liters) without expensive operating machinery. For this reason, a number of non-invasive and/or disposable mixing systems that do not require an external mechanical operation have been developed. Many of these systems work well within certain size ranges, however, problems sometimes arise as larger mixing systems are attempted. Some relevant examples of prior art pneumatic mixing systems include the following.

U.S. Pat. No. 6,032,931, issued to Plunkett, discloses an aeration device for use in a pond. Compressed gas is supplied to a conduit to form bubbles as the gas/air exits from a series of apertures. As the bubbles rise, they drive turbines to rotate and thereby create additional mixing turbulence.

U.S. Pat. No. 6,322,056, issued to Drie describes a submarine type liquid mixer with aeration. The buoyancy shells provide a downwardly facing upwardly concave surface for capturing gas bubbles so as to provide a buoyancy force to the struts. The bubbles may be naturally involved within the liquid due to chemical processes or they may be released from a gas inflow into the tank. As the gases are captured by a series of shells, each in turn is displaced upwardly whereupon the gas is released at the top of tank. At this point, one of the shells loses its buoyancy while the lower shell has received gas bubbles, enabling it to be displaced and thus the motion of the shells is reversed. This up and down cyclic motion of the shells mixes the liquid in the tanks.

U.S. Pat. No. 6,406,624, issued to De Vos discloses a flocculation apparatus and apparatus for floating upwardly in a liquid and for moving downwardly in the liquid under the influence of gravity. The flocculation apparatus includes a paddle apparatus and a flotation and compressed gas discharge apparatus. A pressurized or compressed air line with a branch line extending upwardly into the flotation and compressed gas discharge apparatus is also provided. When gas is introduced through the lines into the gas discharge apparatus, the apparatus becomes increasingly buoyant and floats upwardly in the liquid within the basin and thereby moves the paddle apparatus and frame apparatus upwardly in the liquid as well. When the apparatus reaches the top, the compressed air is released and the frame apparatus along with the paddle apparatus are pulled downwardly in the liquid by gravity. During the upward and downward movement of the paddle members, the paddle members agitate or stir the liquid contained within the basin.

U.S. Pat. No. 6,390,455, issued to Lee et al. describes a bubble generating device having a float connected thereto. The object of the invention is to provide a bubble generating device that can be operated in a desired depth of water which ultimately is used to agitate the water and provide a supply of oxygen to the water. The device includes a porous portion which is connected to a source of air through a pipe to generate bubbles while the float maintains the apparatus at a desired level in a water container.

U.S. Pat. No. 5,645,346, issued to Thuna is directed to a food preparation blender with a rotating and vertically oscillating mixing blade. The blender includes a pressure plate which causes a first shaft to be raised, thus raising the mixing blades while mixing takes place.

U.S. Pat. No. 6,649,117, issued to Familletti discloses an improved reactor/fermentor apparatus useful for carrying out cell culture and fermentation. The apparatus utilizes novel design features to provide optimum agitation of the cells while minimizing mechanical shear force. The reactor is composed of two chambers; an upper, wider chamber and a lower, small diameter chamber which are connected by inwardly sloping side walls. Agitation is accomplished by utilizing a gently flowing centrally disposed gas stream.

U.S. Pat. No. 3,963,581, issued to Giacobbe et al. describes an air lift fermentor comprising in combination a hollow cylindrical body, vertically located and subdivided into three zones by a pair of diaphragms parallel to the axis of said cylindrical body, the central zone of which is destined to fermentation of the liquor, and the two lateral zones serve for recirculating the liquor itself, after its passage through a heat exchanger and an air distributor, both located near the bottom of said cylindrical body.

It is an objective of the present invention to provide a pneumatic bioreactor that is capable of efficiently and thoroughly mixing solutions without contamination. It is a further objective to such a reactor that can be scaled to relatively large sizes using the same technology. It is a still further objective of the invention to a bioreactor that can be produced in a disposable form. It is yet a further objective of the invention to provide a bioreactor that can be accurately controlled by internal pneumatic force, as to speed and mixing force applied to the solution without creating a foaming problem. Finally, it is an objective to provide a bioreactor that is simple and inexpensive to produce and to operate while fulfilling all of the described performance criteria.

While some of the objectives of the present invention are disclosed in the prior art, none of the inventions found include all of the requirements identified.

SUMMARY OF THE INVENTION

The present invention addresses all of the deficiencies of prior art pneumatic bioreactor inventions and satisfies all of the objectives described above.

A pneumatic bioreactor providing all of the desired features can be constructed from the following components. A containment vessel is provided. The vessel has a top, a closed bottom, a surrounding wall and is of sufficient size to contain a fluid to be mixed and a mixing apparatus. The mixing apparatus includes at least one gas supply line. The supply line terminates at an orifice adjacent the bottom of the vessel. At least one buoyancy-driven mixing device is provided. The mixing device moves in the fluid as gas from the supply line is introduced into and vented from the mixing device. When gas is introduced into the gas supply line the gas will enter the mixing device and cause the device to mix the fluid.

In a variant of the invention, the buoyancy-driven mixing device further includes at least one floating mixer. The mixer has a central, gas-holding chamber and a plurality of mixing elements located about the central chamber. The mixing elements are shaped to cause the mixer to agitate the fluid as the mixer rises in the fluid in the containment vessel. The central chamber has a gas-venting valve. The valve permits escape of gas as the central chamber reaches a surface of the fluid. A constraining member is provided. The constraining member limits horizontal movement of the floating mixer as it rises or sinks in the fluid. When gas is introduced into the gas supply line, the gas will enter the gas holding chamber and cause the floating mixer to rise by buoyancy in the fluid while agitating the fluid. When the gas venting valve of the central chamber reaches the surface of the fluid, the gas will be released and the floating mixer will sink toward the bottom of the containment vessel where the central chamber will again be filled with gas, causing the floating mixer to rise.

In another variant, means are provided for controlling a rate of assent of the floating mixer.

In still another variant, the means for controlling the rate of assent of the floating mixer includes a ferromagnetic substance attached to either of the floating mixer or the constraining member and a controllable electromagnet located adjacent the bottom of the containment vessel. The gas flow is interrupted by an on/off switch which is controlled by interactions of two magnetic substances. Therefore, the volume of gas supplied into the gas-holding chamber is determined by the strength of the electromagnetic power since the gas flow stops as the floating device starts to rise when the buoyancy becomes greater than the magnetic holding force.

In yet another variant, the central, gas-holding chamber further includes an opening. The opening is located at an upper end of the chamber. A vent cap is provided. The vent cap is sized and shaped to seal the opening when moved upwardly against it by buoyancy from gas from the supply line. A support bracket is provided. The support bracket is located within the chamber to support the vent cap when it is lowered after release of gas from the chamber. When the chamber rises to the surface of the fluid the vent cap will descend from its weight and the opening will permit the gas to escape, the chamber will then sink in the fluid and the vent cap will again rise due to buoyancy from a small amount of gas permanently enclosed in the vent cap, thereby sealing the opening.

In a further variant, a second floating mixer is provided. A second constraining member is provided, limiting horizontal movement of the second mixer as it rises in the fluid. At least one additional gas supply line is provided. The additional supply line terminates at an orifice adjacent the bottom of the vessel. At least one pulley is provided. The pulley is attached to the bottom of the containment vessel. A flexible member is provided. The flexible member attaches the chamber of the floating mixer to a chamber of the second floating mixer. The flexible member is of a length permitting the gas venting valve of the chamber of the floating mixer to reach the surface of the fluid while the chamber of the second floating mixer is spaced from the bottom of the containment vessel. When the floating mixer is propelled upwardly by buoyancy from the gas from the supply line the second floating mixer is pulled downwardly by the flexible member until the gas is released from the chamber of the floating mixer as its gas venting valve reaches the surface of the fluid. The chamber will then sink in the fluid as the second floating mixer rises by buoyancy from gas introduced from the second supply line.

In yet a further variant, the containment vessel is formed of resilient material, the material is sterilizable by gamma irradiation methods.

In still a further variant, the buoyancy-driven mixing device further includes at least one floating plunger. The plunger has a central, gas-holding chamber and at least one disk located about the central chamber. The disk is shaped to cause the plunger to agitate the fluid as the plunger rises in the fluid in the containment vessel. The central chamber has a gas-venting valve. The valve permits escape of gas as the central chamber reaches a surface of the fluid. A mixing partition is provided. The partition is located in the containment vessel adjacent the floating plunger and has at least one aperture to augment a mixing action of the floating plunger. A constraining member is provided. The constraining member limits horizontal movement of the plunger as it rises or sinks in the fluid. When gas is introduced into the gas supply line the gas will enter the gas holding chamber and cause the floating plunger to rise by buoyancy in the fluid while agitating the fluid. When the gas venting valve of the central chamber reaches the surface of the fluid, the gas will be released and the floating plunger will sink toward the bottom of the containment vessel where the central chamber will again be filled with gas, causing the floating plunger to rise.

In another variant of the invention, a second floating plunger is provided. A second constraining member is provided, limiting horizontal movement of the second plunger as it rises in the fluid. At least one additional gas supply line is provided. The additional supply line terminates at an orifice adjacent the bottom of the vessel. At least one pulley is provided. The pulley is attached to the bottom of the containment vessel. A flexible member is provided. The flexible member attaches the chamber of the floating plunger to a chamber of the second floating plunger. The flexible member is of a length permitting the gas venting valve of the chamber of the floating plunger to reach the surface of the fluid while the chamber of the second floating plunger is spaced from the bottom of the containment vessel. The mixing partition is located between the floating plunger and the second floating plunger. When the floating plunger is propelled upwardly by buoyancy from the gas from the supply line the second floating plunger is pulled downwardly by the flexible member until the gas is released from the chamber of the floating plunger as its gas venting valve reaches the surface of the fluid. The chamber will then sink in the fluid as the second floating plunger rises by buoyancy from gas introduced from the second supply line.

In still another variant, the pneumatic bioreactor further includes a cylindrical chamber. The chamber has an inner surface, an outer surface, a first end, a second end and a central axis. At least one mixing plate is provided. The mixing plate is attached to the inner surface of the chamber. First and second flanges are provided. The flanges are mounted to the cylindrical chamber at the first and second ends, respectively. First and second pivot points are provided. The pivot points are attached to the first and second flanges, respectively and to the containment vessel, thereby permitting the cylindrical chamber to rotate about the central axis. A plurality of gas holding members are provided. The members extend from the first flange to the second flange along the outer surface of the cylindrical chamber and are sized and shaped to entrap gas bubbles from the at least one gas supply line. The gas supply line terminates adjacent the cylindrical chamber on a first side of the chamber below the gas holding members. When gas is introduced into the containment vessel through the supply line it will rise in the fluid and gas bubbles will be entrapped by the gas holding members. This will cause the cylindrical chamber to rotate on the pivot points in a first direction and the at least one mixing plate to agitate the fluid.

In yet another variant, a rate of rotation of the cylindrical chamber is controlled by varying a rate of introduction of gas into the gas supply line.

In a further variant, a second gas supply line is provided. The second supply line terminates adjacent the cylindrical chamber on a second, opposite side of the chamber below the gas holding members. Gas from the second supply line causes the cylindrical chamber to rotate on the pivot points in a second, opposite direction.

In still a further variant, the at least one mixing plate has at least one aperture to augment mixing of the fluid in the containment vessel.

In yet a further variant, the containment vessel further includes a closable top. The top has a vent, permitting the escape of gas from the gas supply line through a sterile filter.

In another variant of the invention, a temperature control jacket is provided. The jacket surrounds the containment vessel.

In yet another variant, a pneumatic bioreactor includes a containment vessel. The vessel has a top, a closed bottom, a surrounding wall and is of sufficient size to contain a fluid to be mixed and a mixing apparatus. The mixing apparatus includes at least one gas supply line. The supply line terminates at an orifice at the bottom of the vessel. At least one floating impeller is provided. The impeller has a central, gas-containing chamber and a plurality of impeller blades arcurately located about the central chamber. The impeller blades are shaped to cause the impeller to revolve about a vertical axis as the impeller rises in fluid in the containment vessel.

The central chamber has a gas-venting valve. The valve permits escape of gas as the central chamber reaches a surface of the fluid. An outside housing is provided. The housing is ring-shaped and surrounds the floating impeller and constrains its lateral movement. At least one supporting pole is provided. The pole extends from the bottom upwardly toward the top. The outside housing is slidably attached to the supporting pole. The floating impeller is rotatably attached to the outside housing. When gas is introduced into the gas supply line the gas will enter the gas containing chamber and cause the floating impeller to rise in the fluid while rotating and mixing the fluid. When the gas venting valve of the central chamber reaches the surface of the fluid, the gas will be released and the floating impeller will sink toward the bottom of the containment vessel where the central chamber will again be filled with gas, causing the floating impeller to rise.

In still another variant, the impeller blades are rotatably mounted to the central chamber and the central chamber is fixedly attached to the outside housing.

In a further variant, the impeller blades are fixedly mounted to the central chamber and rotatably mounted to the outside housing.

In still a further variant, the outside housing further includes a horizontal interior groove located on an inner surface of the housing. The impeller blades include a projection, sized and shaped to fit slidably within the groove.

In yet a further variant, means are provided for controlling a rate of assent of the floating impeller.

In another variant of the invention, the means for controlling a rate of assent of the floating impeller includes a ferromagnetic substance attached to either the floating impeller or the outside housing and a controllable electromagnet located adjacent the bottom of the containment vessel.

In still another variant, the central, gas-containing chamber further includes an opening located at an upper end of the chamber. A vent cap is provided. The vent cap is sized and shaped to seal the opening when moved upwardly against it by pressure from gas from the supply line. A support bracket is provided. The support bracket is located within the chamber to support the vent cap when it is lowered after release of gas from the chamber. When the chamber rises to the surface of the fluid the vent cap will descend from its weight and the opening will permit the gas to escape. The chamber will then sink in the fluid and the vent cap will again rise due to pressure from gas introduced into the chamber from the gas line, thereby sealing the opening.

In yet another variant, the vent cap further includes an enclosed gas cell. The cell causes the cap to float in the fluid and thereby to reseal the opening after the gas has been released when the chamber reached the surface of the fluid.

In a further variant, the pneumatic bioreactor further includes a second floating impeller. A second outside housing surrounding the second floating impeller is provided. At least one additional supporting pole is provided. At least one additional gas supply line is provided. The additional supply line terminates at an orifice at the bottom of the vessel. The second outside housing is slidably attached to the additional supporting pole. The second floating impeller is rotatably attached to the second outside housing. At least one pulley is provided. The pulley is attached to the bottom of the containment vessel.

A flexible member is provided. The flexible member attaches the chamber of the floating impeller to a chamber of the second floating impeller. The flexible member is of a length to permit the gas venting valve of the chamber of the floating impeller to reach the surface of the fluid while the chamber of the second floating impeller is spaced from the bottom of the containment vessel. When the floating impeller is propelled upwardly by pressure from the gas from the supply line the second floating impeller will be pulled downwardly by the flexible member until the gas is released from the chamber of the floating impeller as its gas venting valve reaches the surface of the fluid, the chamber will then sink in the fluid as the second floating impeller rises under pressure from gas introduced from the second supply line.

An appreciation of the other aims and objectives of the present invention and an understanding of it may be achieved by referring to the accompanying drawings and the detailed description of a preferred embodiment.

DESCRIPTION OF THE DRAWINGS

FIG. 1 is a perspective view of a first embodiment of the invention illustrating floating impellers and their control mechanisms;

FIG. 2 is a top view of the FIG. 1 embodiment illustrating the floating chamber affixed to the constraining member with the impeller blades rotating upon the chamber;

FIG. 5 is a perspective view of a second embodiment of the invention illustrating floating plungers and their control mechanisms;

FIG. 6 is a top view of the FIG. 5 embodiment illustrating the floating plungers;

DETAILED DESCRIPTION

Figure 3:
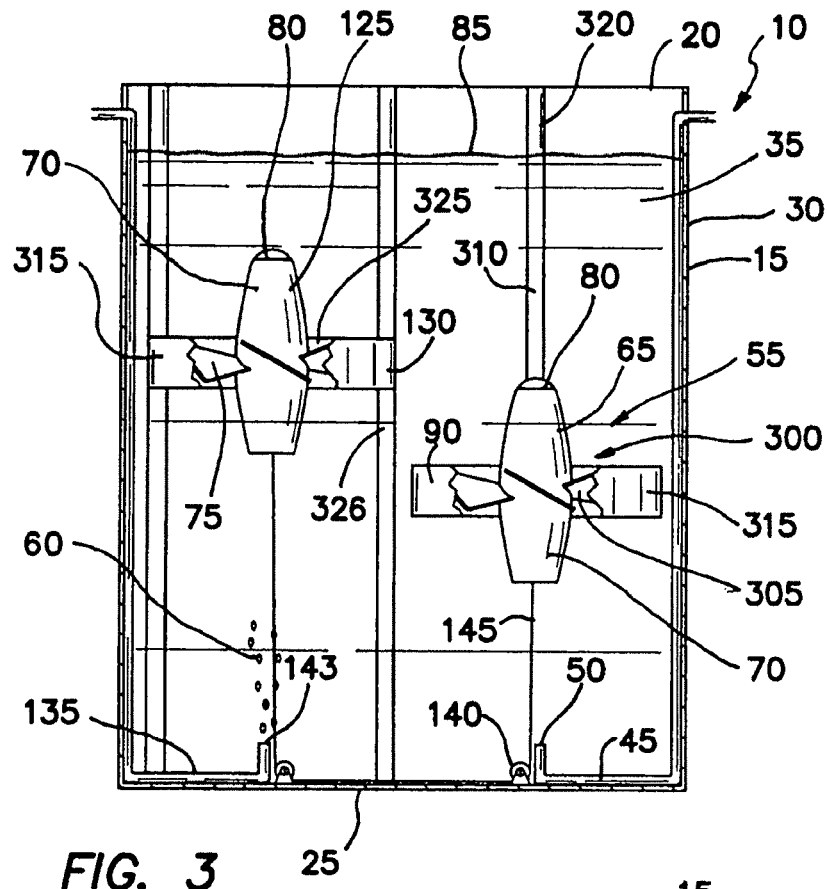
FIG. 3 is a side elevational view of the FIG. 1 embodiment.

A pneumatic bioreactor 10, as illustrated in FIGS. 1-3, providing all of the desired features can be constructed from the following components. A containment vessel 15 is provided. The vessel 15 has a top 20, a closed bottom 25, a surrounding wall 30 and is of sufficient size to contain a fluid 35 to be mixed and a mixing apparatus 40. The mixing apparatus 40 includes at least one gas supply line 45. The supply line 45 terminates at an orifice 50 adjacent the bottom 25 of the vessel 15. At least one buoyancy-driven mixing device 55 is provided. The mixing device 55 moves in the fluid 35 as gas 60 from the supply line 45 is introduced into and vented from the mixing device 55. When gas 60 is introduced into the gas supply line 45 the gas 60 will enter the mixing device 55 and cause the device to mix the fluid 35.

Figure 8:
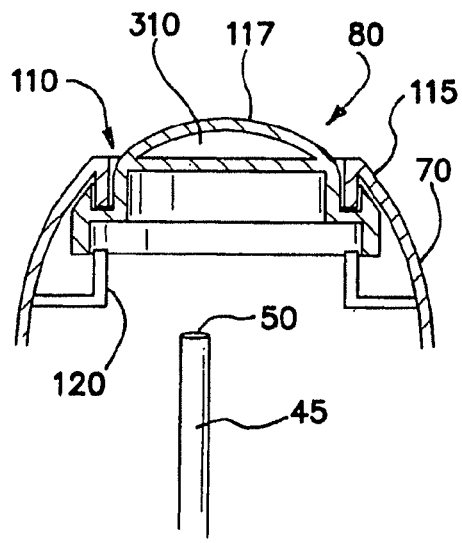
FIG. 8 is a cross-sectional side elevation of the floating chamber illustrating the vent cap in a closed position.
Figure 9:
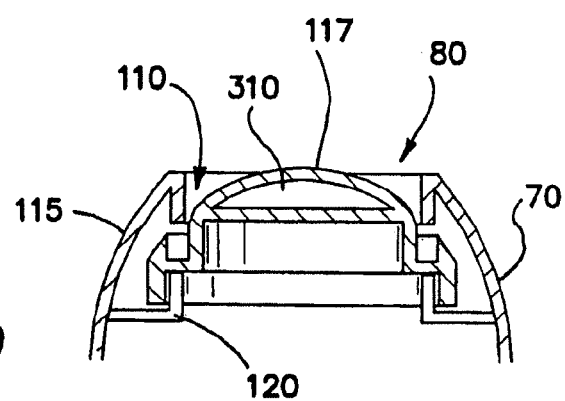
FIG. 9 is a cross-sectional side elevation of the floating chamber illustrating the vent cap in an open position.

In a variant of the invention, the buoyancy-driven mixing device 55 further includes at least one floating mixer 65. The mixer 65 has a central, gas-holding chamber 70 and a plurality of mixing elements 75 located about the central chamber 70. The mixing elements 75 are shaped to cause the mixer 65 to agitate the fluid 35 as the mixer 65 rises in the fluid 35 in the containment vessel 15. The central chamber 70, as illustrated in FIGS. 8 and 9, has a gas-venting valve 80. The valve 80 permits escape of gas 60 as the central chamber 70 reaches a surface 85 of the fluid 35. A constraining member 90 is provided. The constraining member 90 limits horizontal movement of the floating mixer 65 as it rises or sinks in the fluid 35. When gas 60 is introduced into the gas supply line 45, the gas 60 will enter the gas holding chamber 70 and cause the floating mixer 65 to rise by buoyancy in the fluid 35 while agitating the fluid 35. When the gas venting valve 80 of the central chamber 70 reaches the surface 85 of the fluid 35, the gas 60 will be released and the floating mixer 65 will sink toward the bottom 25 of the containment vessel 15 where the central chamber 70 will again be filled with gas 60, causing the floating mixer 65 to rise.

Figure 7:
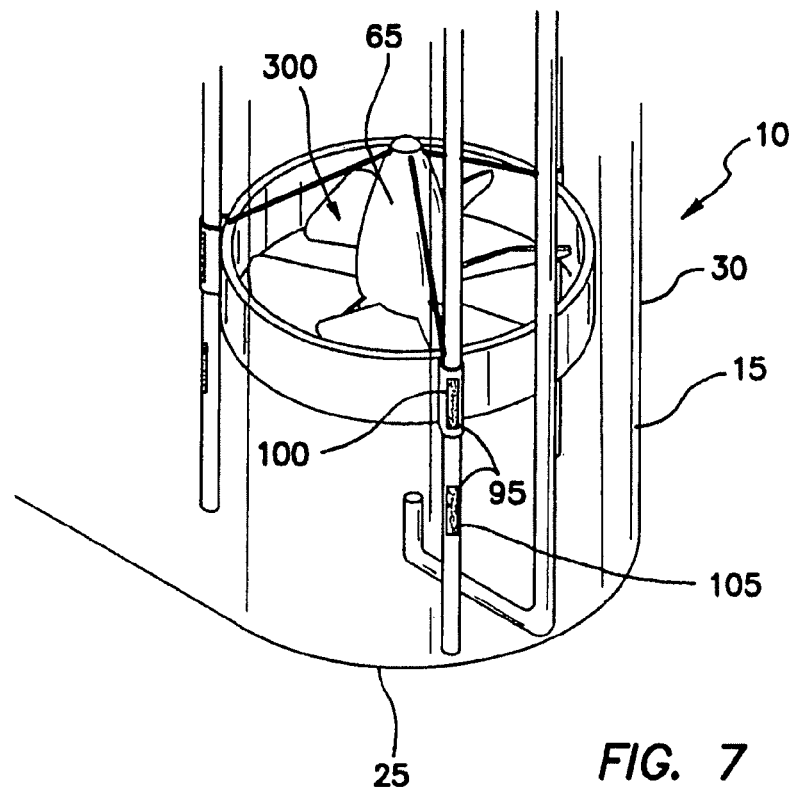
FIG. 7 is a perspective view of the gas supply line and magnetic assent control mechanism.

In another variant, means 95, as illustrated in FIG. 7, are provided for controlling a rate of assent of the floating mixer 65.

In still another variant, the means 95 for controlling the rate of assent of the floating mixer 65 includes a ferromagnetic substance 100 attached to either of the floating mixer 65 or the constraining member 90 and a controllable electromagnet 105 located adjacent the bottom 25 of the containment vessel 15.

In yet another variant, as illustrated in FIGS. 8 and 9, the central, gas-holding chamber 70 further includes an opening 110. The opening 110 is located at an upper end 115 of the chamber 70. A vent cap 117 is provided. The vent cap 117 is sized and shaped to seal the opening 110 when moved upwardly against it by buoyancy from gas 60 from the supply line 45. A support bracket 120 is provided. The support bracket 120 is located within the chamber 70 to support the vent cap 115 when it is lowered after release of gas 60 from the chamber 70. When the chamber 70 rises to the surface 85 of the fluid 35 the vent cap 115 will descend from its weight and the opening 110 will permit the gas 60 to escape, the chamber 70 will then sink in the fluid 35 and the vent cap 115 will again rise due to buoyancy from a small amount of gas 60 permanently enclosed in the vent cap 115, thereby sealing the opening 110.

In a further variant, as illustrated in FIGS. 1-3, a second floating mixer 125 is provided. A second constraining member 130 is provided, limiting horizontal movement of the second mixer 125 as it rises in the fluid 35. At least one additional gas supply line 135 is provided. The additional supply line 135 terminates at an orifice 143 adjacent the bottom 25 of the vessel 15. At least one pulley 140 is provided. The pulley 140 is attached to the bottom 25 of the containment vessel 15. A flexible member 145 is provided. The flexible member 145 attaches the chamber 70 of the floating mixer 65 to a chamber 150 of the second floating mixer 125. The flexible member 145 is of a length permitting the gas venting valve 80 of the chamber 70 of the floating mixer 65 to reach the surface 85 of the fluid 35 while the chamber 70 of the second floating mixer 125 is spaced from the bottom 25 of the containment vessel 15. When the floating mixer 65 is propelled upwardly by buoyancy from the gas 60 from the supply line 45 the second floating mixer 125 is pulled downwardly by the flexible member 145 until the gas 60 is released from the chamber 70 of the floating mixer 65 as its gas venting valve 80 reaches the surface 85 of the fluid 35. The chamber 70 will then sink in the fluid 35 as the second floating mixer 125 rises by buoyancy from gas 60 introduced from the second supply line 135.

In yet a further variant, the containment vessel 15 is formed of resilient material 155, the material is sterilizable by gamma irradiation methods.

In still a further variant, as illustrated in FIGS. 5 and 6, the buoyancy-driven mixing device 10 further includes at least one floating plunger 160. The plunger 160 has a central, gas-holding chamber 70 and at least one disk 165 located about the central chamber 70. The disk 165 is shaped to cause the plunger 160 to agitate the fluid 35 as the plunger 160 rises in the fluid 35 in the containment vessel 15. The central chamber 70 has a gas-venting valve 80. The valve 80 permits escape of gas 60 as the central chamber 70 reaches a surface 85 of the fluid 35. A mixing partition 170 is provided. The partition 170 is located in the containment vessel 15 adjacent the floating plunger 160 and has at least one aperture 175 to augment a mixing action of the floating plunger 160. A constraining member 180 is provided. The constraining member 180 limits horizontal movement of the plunger 160 as it rises or sinks in the fluid 35. When gas 60 is introduced into the gas supply line 45 the gas 60 will enter the gas holding chamber 70 and cause the floating plunger 160 to rise by buoyancy in the fluid 35 while agitating the fluid 35. When the gas venting valve 80 of the central chamber 70 reaches the surface 85 of the fluid 35, the gas 60 will be released and the floating plunger 160 will sink toward the bottom 25 of the containment vessel 15 where the central chamber 70 will again be filled with gas 60, causing the floating plunger 160 to rise.

In another variant of the invention, a second floating plunger 185 is provided. A second constraining member 190 is provided, limiting horizontal movement of the second plunger 185 as it rises in the fluid 35. At least one additional gas supply line 135 is provided. The additional supply line 135 terminates at an orifice 143 adjacent the bottom 25 of the vessel 15. At least one pulley 140 is provided. The pulley 140 is attached to the bottom 25 of the containment vessel 15. A flexible member 145 is provided. The flexible member 145 attaches the chamber 70 of the floating plunger 160 to a chamber of the second floating plunger 185. The flexible member 145 is of a length permitting the gas venting valve 80 of the chamber 70 of the floating plunger 160 to reach the surface 85 of the fluid 35 while the chamber 70 of the second floating plunger 185 is spaced from the bottom 25 of the containment vessel 15. The mixing partition 170 is located between the floating plunger 160 and the second floating plunger 185. When the floating plunger 160 is propelled upwardly by buoyancy from the gas 60 from the supply line 45 the second floating plunger 185 is pulled downwardly by the flexible member 145 until the gas 60 is released from the chamber 70 of the floating plunger 160 as its gas venting valve 80 reaches the surface 85 of the fluid 30. The floating plunger 160 will then sink in the fluid 35 as the second floating plunger 185 rises by buoyancy from gas 60 introduced from the second supply line 135.

In still another variant, as illustrated in FIGS. 10-13, the pneumatic bioreactor 10 further includes a cylindrical chamber 195. The chamber 195 has an inner surface 200, an outer surface 205, a first end 210, a second end 215 and a central axis 220. At least one mixing plate 225 is provided. The mixing plate 225 is attached to the inner surface 200 of the chamber 195. First 230 and second 235 flanges are provided. The flanges 230, 235 are mounted to the cylindrical chamber 195 at the first 210 and second ends 215, respectively. First 240 and second 245 pivot points are provided. The pivot points 240, 245 are attached to the first 230 and second 235 flanges, respectively and to the containment vessel 15, thereby permitting the cylindrical chamber 195 to rotate about the central axis 220. A plurality of gas holding members 250 are provided. The members 250 extend from the first flange 230 to the second flange 235 along the outer surface 205 of the cylindrical chamber 195 and are sized and shaped to entrap gas bubbles 255 from the at least one gas supply line 45. The gas supply line 45 terminates adjacent the cylindrical chamber 195 on a first side 260 of the chamber 195 below the gas holding members 250. When gas 60 is introduced into the containment vessel 15 through the supply line 45 it will rise in the fluid 35 and gas bubbles 255 will be entrapped by the gas holding members 250. This will cause the cylindrical chamber 195 to rotate on the pivot points 240, 245 in a first direction 262 and the at least one mixing plate 225 to agitate the fluid 35.

In yet another variant, a rate of rotation of the cylindrical chamber 195 is controlled by varying a rate of introduction of gas 60 into the gas supply line 45.

Figure 12:
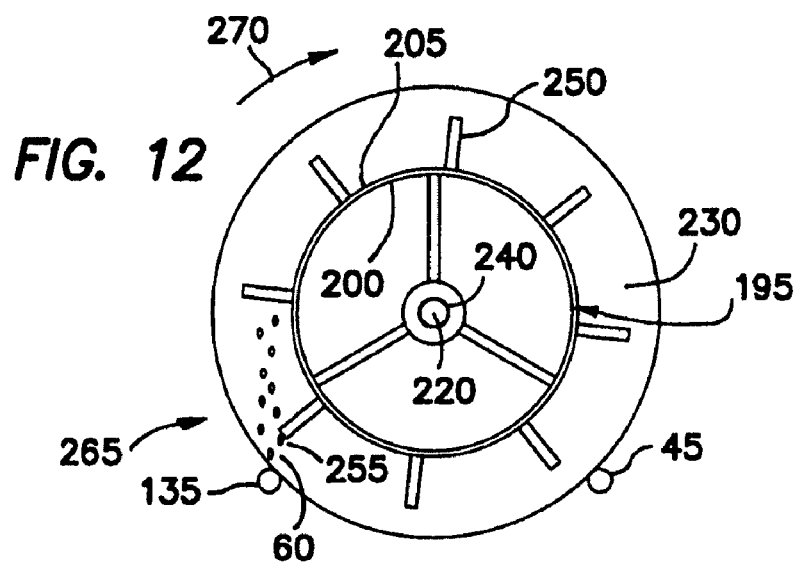
FIG. 12 is an end view of the FIG. 10 embodiment illustrating a pair of gas supply lines.

In a further variant, as illustrated in FIG. 12, a second gas supply line 135 is provided. The second supply line 135 terminates adjacent the cylindrical chamber 195 on a second, opposite side 265 of the chamber 195 below the gas holding members 250. Gas 60 from the second supply line 135 causes the cylindrical chamber 195 to rotate on the pivot points 240,245 in a second, opposite direction 270.

Figure 10:
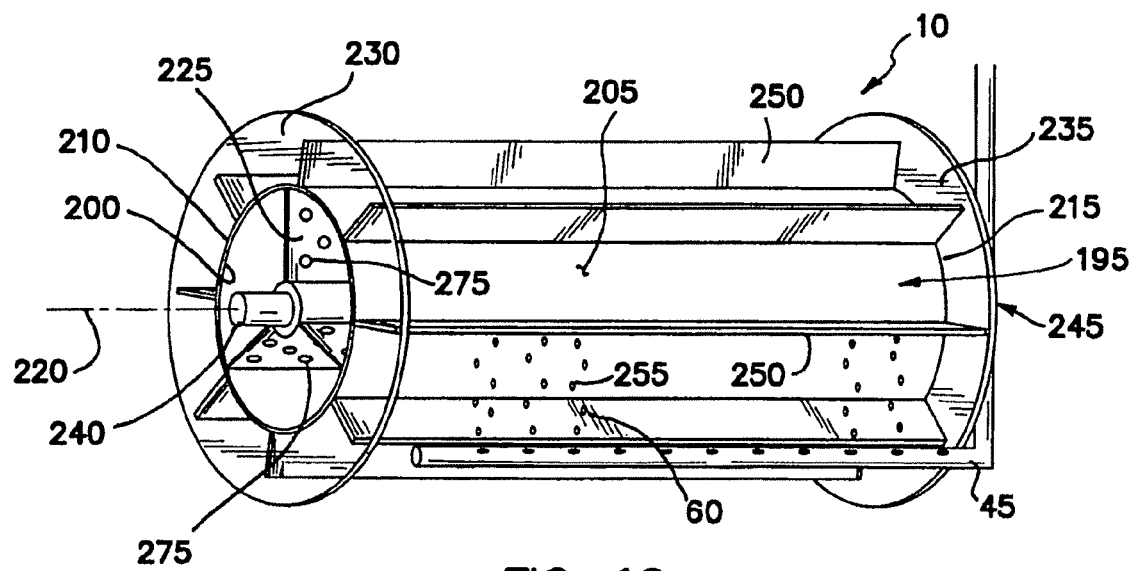
FIG. 10 is a perspective view of a third embodiment of the invention illustrating a rotating drum mixer with gas supply line.
Figure 11:
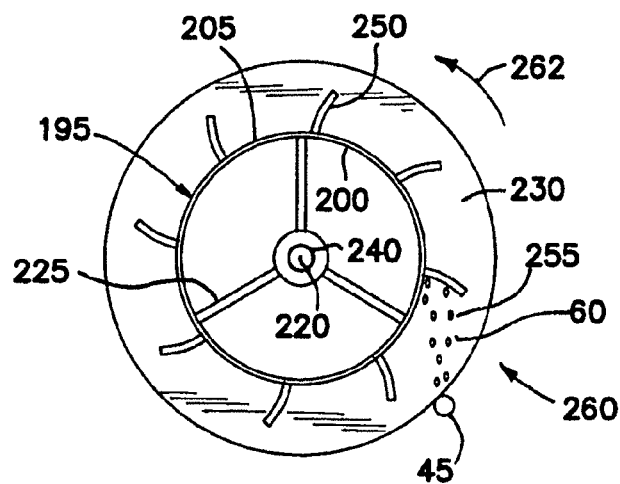
FIG. 11 is an end view of the FIG. 10 embodiment illustrating a single gas supply line.
Figure 13:
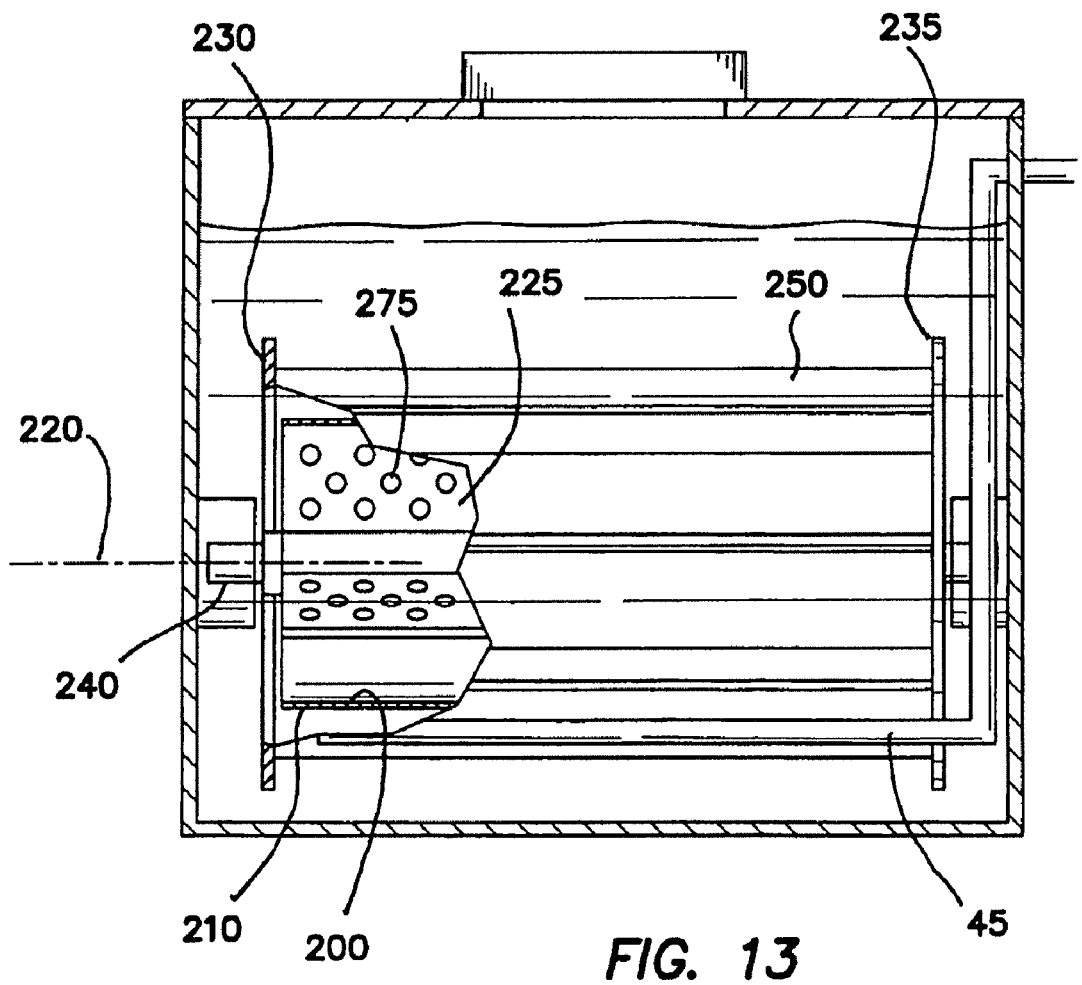
FIG. 13 is a side elevational view of the FIG. 10 embodiment illustrating a containment vessel.

In still a further variant, as illustrated in FIGS. 10 and 13, the at least one mixing plate 225 has at least one aperture 275 to augment mixing of the fluid 35 in the containment vessel 15.

Figure 14:
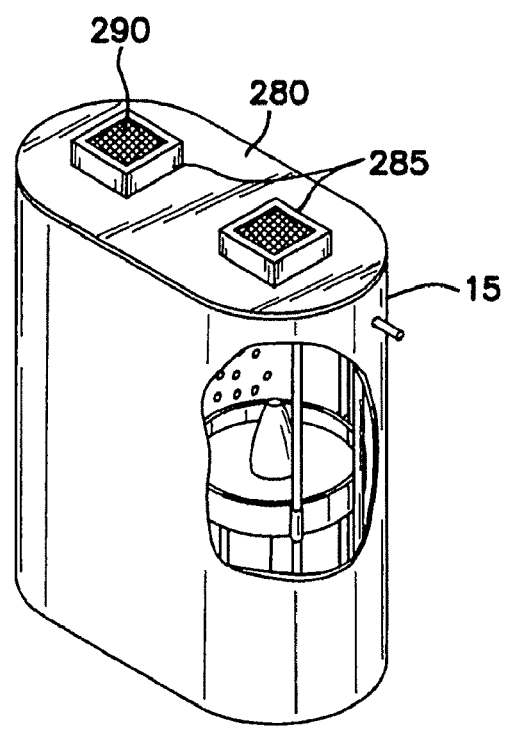
FIG. 14 is a perspective view of the FIG. 5 embodiment illustrating a closable top and sterile filters.

In yet a further variant, as illustrated in FIG. 14, the containment vessel 15 further includes a closable top 280. The top has a vent 285, permitting the escape of gas 60 from the gas supply line 45 through a sterile filter 290.

Figure 15:
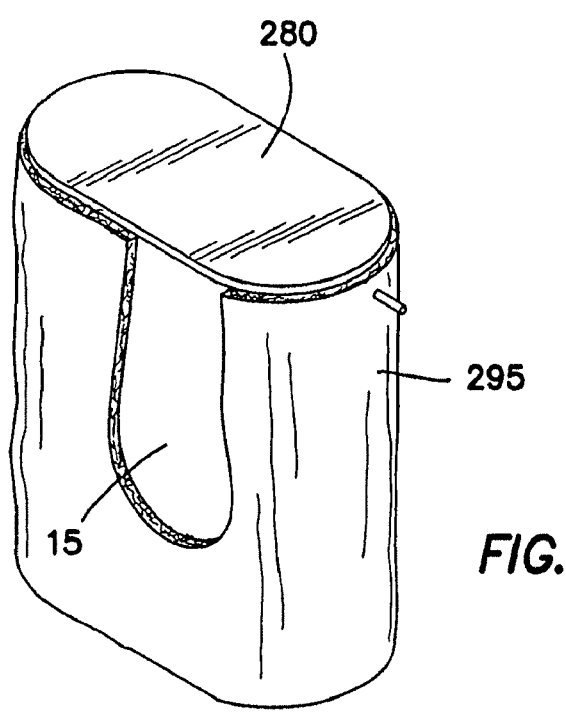
FIG. 15 is a perspective view of the FIG. 5 embodiment illustrating a temperature control jacket surrounding the vessel.

In another variant of the invention, as illustrated in FIG. 15, a temperature control jacket 295 is provided. The jacket 295 surrounds the containment vessel 15.

In yet another variant, as illustrated in FIGS. 1-3, a pneumatic bioreactor 10 includes a containment vessel 15. The vessel 15 has a top 20, a closed bottom 25, a surrounding wall 30 and is of sufficient size to contain a fluid 35 to be mixed and a mixing apparatus 40. The mixing apparatus 40 includes at least one gas supply line 45. The supply line 45 terminates at an orifice 50 at the bottom 25 of the vessel 15. At least one floating impeller 300 is provided. The impeller 300 has a central, gas-containing chamber 70 and a plurality of impeller blades 305 arcuately located about the central chamber 70. The impeller blades 305 are shaped to cause the impeller 300 to revolve about a vertical axis 310 as the impeller 300 rises in fluid 35 in the containment vessel 15.

The central chamber 70 has a gas-venting valve 80. The valve 80 permits escape of gas 60 as the central chamber 70 reaches a surface 85 of the fluid 35. An outside housing 315 is provided. The housing 315 is ring-shaped and surrounds the floating impeller 300 and constrains its lateral movement. At least one supporting pole 320 is provided. The pole 320 extends from the bottom 25 upwardly toward the top 20. The outside housing 315 is slidably attached to the supporting pole 320. The floating impeller 300 is rotatably attached to the outside housing 315. When gas 60 is introduced into the gas supply line 45 the gas 60 will enter the gas containing chamber 70 and cause the floating impeller 300 to rise in the fluid 35 while rotating and mixing the fluid 35. When the gas venting valve 80 of the central chamber 70 reaches the surface 85 of the fluid 35, the gas 60 will be released and the floating impeller 300 will sink toward the bottom 25 of the containment vessel 15 where the central chamber 70 will again be filled with gas 60, causing the floating impeller 300 to rise.

Figure 4:
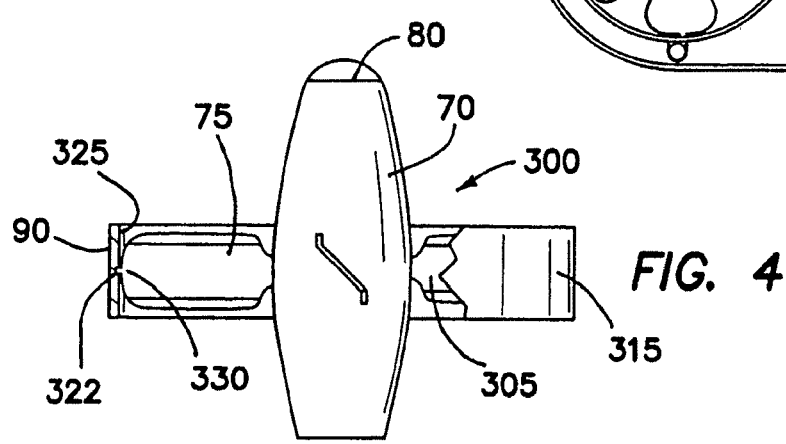
FIG. 4 is a side elevational view of the FIG. 2A embodiment of the floating impeller.
Figure 4A:
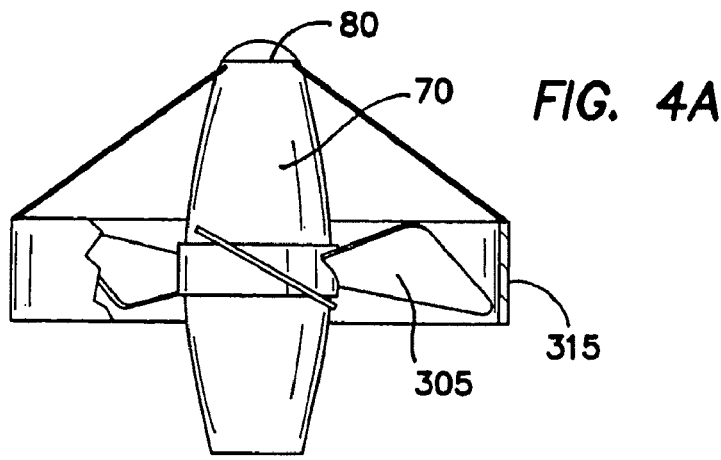
FIG. 4A is a side elevational view of the FIG. 2 embodiment of the floating impeller.

In still another variant, as illustrated in FIGS. 2 and 4A, the impeller blades 305 are rotatably mounted to the central chamber 70 and the central chamber 70 is fixedly attached to the outside housing 315.

Figure 2A:
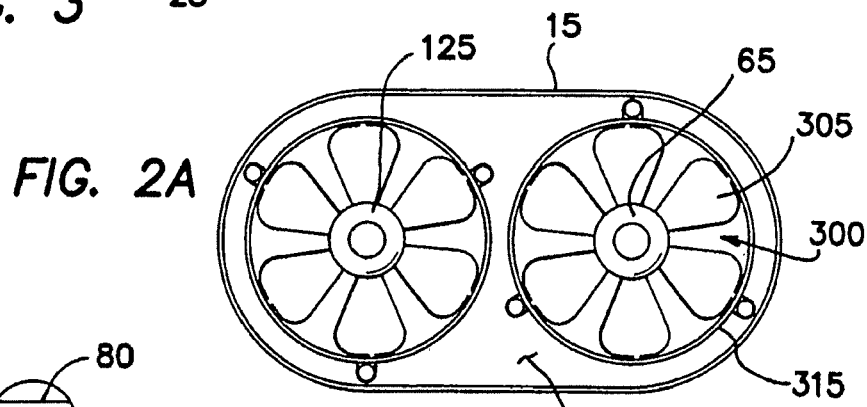
FIG. 2A is a top view of the FIG. 1 embodiment illustrating the floating chamber rotating within the constraining member with the impeller blades fixed to the chamber.

In a further variant, as illustrated in FIGS. 2A and 4, the impeller blades 305 are fixedly mounted to the central chamber 70 and rotatably mounted to the outside housing 315.

In still a further variant, the outside housing 315 further includes a horizontal interior groove 322 located on an inner surface 325 of the housing 315. The impeller blades 305 include a projection 330, sized and shaped to fit slidably within the groove 322.

In yet a further variant, as illustrated in FIG. 7, means 95 are provided for controlling a rate of assent of the floating impeller 300.

In another variant of the invention, the means 95 for controlling a rate of assent of the floating impeller 300 includes a ferromagnetic substance 100 attached to either the floating impeller 300 or the outside housing 315 and a controllable electromagnet 105 located adjacent the bottom 25 of the containment vessel 15.

In still another variant, as illustrated in FIGS. 8 and 9, the central, gas-containing chamber 70 further includes an opening 110 located at an upper end 115 of the chamber 70. A vent cap 115 is provided. The vent cap 115 is sized and shaped to seal the opening 110 when moved upwardly against it by pressure from gas 60 from the supply line 45. A support bracket 120 is provided. The support bracket 120 is located within the chamber 70 to support the vent cap 115 when it is lowered after release of gas 60 from the chamber 70. When the chamber 70 rises to the surface of the fluid 35 the vent cap 115 will descend from its weight and the opening 110 will permit the gas 60 to escape. The floating impeller 300 will then sink in the fluid 35 and the vent cap 115 will again rise due to pressure from gas 60 introduced into the chamber 70 from the gas line 45, thereby sealing the opening 110.

In yet another variant, the vent cap 115 further includes an enclosed gas cell 310. The cell 310 causes the cap 115 to float in the fluid 35 and thereby to reseal the opening 110 after the gas 60 has been released when the chamber 70 reached the surface 85 of the fluid 35.

In a further variant, as illustrated in FIGS. 1 and 3, the pneumatic bioreactor 10 further includes a second floating impeller 317. A second outside housing 324 surrounding the second floating impeller 317 is provided. At least one additional supporting pole 326 is provided. At least one additional gas supply line 135 is provided. The additional supply line 135 terminates at an orifice 143 at the bottom 25 of the vessel 15. The second outside housing 324 is slidably attached to the additional supporting pole 325. The second floating impeller 317 is rotatably attached to the second outside housing 324. At least one pulley 140 is provided. The pulley 140 is attached to the bottom 25 of the containment vessel 15.

A flexible member 145 is provided. The flexible member 145 attaches the chamber 70 of the floating impeller 300 to a chamber 70 of the second floating impeller 317. The flexible member 145 is of a length to permit the gas venting valve 80 of the chamber 70 of the floating impeller 300 to reach the surface 85 of the fluid 35 while the chamber 70 of the second floating impeller 317 is spaced from the bottom 25 of the containment vessel 15. When the floating impeller 300 is propelled upwardly by pressure from the gas 60 from the supply line 45 the second floating impeller 315 will be pulled downwardly by the flexible member 145 until the gas 60 is released from the chamber 70 of the floating impeller 300 as its gas venting valve 80 reaches the surface 85 of the fluid 35, the floating impeller 300 will then sink in the fluid 35 as the second floating impeller 315 rises under pressure from gas 60 introduced from the second supply line 135.

An appreciation of the other aims and objectives of the present invention and an understanding of it may be achieved by referring to the accompanying drawings and the detailed description of a preferred embodiment.

The invention claimed is:

1. A pneumatic bioreactor comprising:
   a containment vessel formed from a resilient material;
   at least one gas supply line in communication with said vessel; and
   at least one buoyancy-driven mixing device comprising:
      a mixing wheel mounted within said containment vessel so as to be rotatable about a substantially horizontal, central axis;
      a plurality of gas trapping members extending along an outer periphery of said wheel, wherein said gas supply line terminates below said gas trapping members and wherein said gas trapping members are configured to entrap rising gas bubbles introduced into said containment vessel through said gas supply line to thereby cause said mixing wheel to rotate about said central axis in a first direction; and
      at least one mixing vane disposed radially inwardly from said gas trapping members and extending axially with respect to said central axis so as to be configured to agitate fluid contained in said containment vessel as said mixing wheel rotates about said central axis.

2. The pneumatic bioreactor of claim 1, further comprising at least one aperture formed in said mixing vane.

3. The pneumatic bioreactor of claim 1, comprising two gas supply lines terminating below opposite sides of said mixing wheel configured for causing rotation of said mixing wheel in opposite directions by introduction of gas into said containment vessel through one or the other of said gas supply lines.

4. The pneumatic bioreactor of claim 1, wherein said gas supply line is configured to enable selective control of the rate of introduction of gas into said containment vessel for selectively controlling the speed of rotation of said mixing wheel.

5. The pneumatic bioreactor of claim 1, wherein the containment vessel comprises a closable top and a top vent permitting escape of gas introduced into said containment vessel.

6. The pneumatic bioreactor of claim 5, further comprising a filter associated with said top vent.

7. The pneumatic bioreactor of claim 1, further comprising a temperature control jacket configured to control the temperature of the contents of said containment vessel.

8. The pneumatic bioreactor of claim 1, wherein said mixing vane comprises a mixing plate.

9. The pneumatic bioreactor of claim 8, wherein said mixing plate extends radially inward from an inner periphery of said mixing wheel.

10. The pneumatic bioreactor of claim 9, wherein said mixing vane extends radially inward from an inner periphery of said mixing wheel to said central axis.

11. The pneumatic bioreactor of claim 1, wherein said containment vessel is a sterile containment vessel.

* * * * *